United States Patent
Spoljaric

(10) Patent No.: US 7,644,818 B2
(45) Date of Patent: Jan. 12, 2010

(54) PLASTER DISPENSER

(75) Inventor: Davorin Spoljaric, Helsinki (FI)

(73) Assignee: Cederroth International AB, Upplands Vasby (SE)

( * ) Notice: Subject to any disclaimer, the term of this patent is extended or adjusted under 35 U.S.C. 154(b) by 271 days.

(21) Appl. No.: 11/795,497

(22) PCT Filed: Dec. 16, 2005

(86) PCT No.: PCT/SE2005/001942

§ 371 (c)(1),
(2), (4) Date: Jul. 18, 2007

(87) PCT Pub. No.: WO2006/078201

PCT Pub. Date: Jul. 27, 2006

(65) Prior Publication Data

US 2009/0120826 A1    May 14, 2009

(30) Foreign Application Priority Data

Jan. 20, 2005 (SE) .................... 0500144

(51) Int. Cl.
*A61L 15/00* (2006.01)
*A47F 1/04* (2006.01)

(52) U.S. Cl. .................. 206/441; 206/233; 221/34; 221/303

(58) Field of Classification Search .................. 206/233, 206/440, 441; 221/25, 34, 65, 247–249, 221/92, 303–309; 248/309.1
See application file for complete search history.

(56) References Cited

U.S. PATENT DOCUMENTS

| 3,189,219 | A | | 6/1965 | Holzworth et al. |
| 3,530,494 | A | * | 9/1970 | Baratta ........................ 206/441 |
| 3,899,077 | A | | 8/1975 | Spiegelberg |
| 4,194,624 | A | | 3/1980 | Spiegelberg |
| 4,735,342 | A | * | 4/1988 | Goldstein ..................... 221/25 |
| 6,050,413 | A | * | 4/2000 | Benedetti ..................... 206/440 |
| 6,662,967 | B2 | * | 12/2003 | Roy ............................ 206/441 |
| 6,918,488 | B2 | * | 7/2005 | Renhed ........................ 206/440 |
| 6,923,320 | B2 | * | 8/2005 | Grossman .................... 206/440 |
| 7,104,420 | B2 | * | 9/2006 | Maffei ......................... 206/440 |
| 7,147,129 | B1 | * | 12/2006 | Menefield .................... 206/440 |
| 7,506,760 | B2 | * | 3/2009 | Grossman .................... 206/440 |
| 2004/0232013 | A1 | | 11/2004 | Renhed |

FOREIGN PATENT DOCUMENTS

EP    0 948 949 A2    10/1999

* cited by examiner

Primary Examiner—Bryon P Gehman
(74) Attorney, Agent, or Firm—Young & Thompson

(57) ABSTRACT

A plaster dispenser (1) for removing plasters (3) individually from a plaster pack (2) that includes a number of plasters (3), each inserted in a plastic or paper pocket, wherein the pockets are directed in mutually the same direction, and are together surrounded by a folded plastic or paper sheet (4a, 4b) whose first edge (5) extends at right angles to the longitudinal direction of respective plaster accommodating pockets, the plaster pack (2) being widened from the first edge (5) in a direction towards two mutually opposing second edges (19a, 19b) of the sheet parts, and wherein the dispenser (1) including a box-shaped space (6).

20 Claims, 1 Drawing Sheet

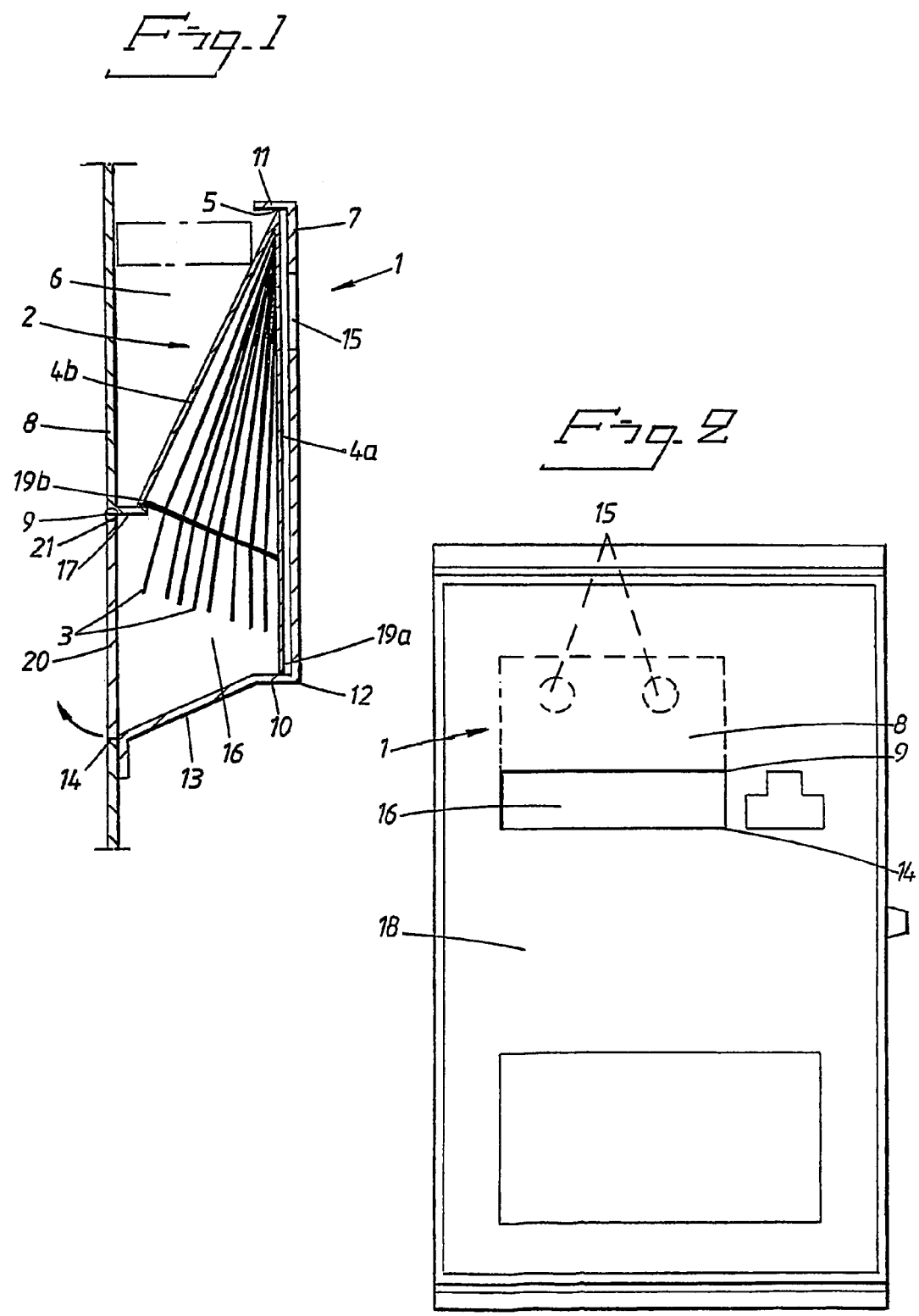

PLASTER DISPENSER

The present invention relates to a plaster dispenser that has a plaster pack placed therein.

It is at present normal to provide in workplaces, for instance, a plaster container, such as a plaster dispenser from Cederroth International AB, Sweden, in a location where personnel can find plasters quickly and easily in the event of an injury. Plaster packs are stored for replacing empty plaster packs. Thus, when a pack or packs has/have been emptied of its/their contents, the empty pack/packs can be exchange for fresh ones. The plasters will typically include two protective plastic strips which protect the two adhesive parts of the plaster that are intended to be applied to the skin of a patient when used. That part of the plaster which is intended to be placed over the actual wound or injury is located between the two adhesive parts of the plaster. The plaster pack mentioned above includes plaster protective parts which are placed against the plaster prior to its use. One-half of the plaster, including its protective cover, is inserted down into a respective plastic or paper pockets included in the pack. When the plaster shall be used, it is withdrawn from its respective plastic or paper pockets. The protective covering that is inserted in the pack is peeled away from the plaster and left in the pack.

In the case of Salvequick® plaster dispenser, available from Cederroth International AB, Sweden, the plaster packs can be renewed with the aid of a key that is specific to these particular plaster dispensers. A Salvequick® plaster dispenser can be mounted in a location where it is clearly visible to the personnel in the workplace, for instance it may be mounted directly on a wall or on a first-aid board, a first-aid board that includes a protective covering, or a first-aid cabinet, box or a technically corresponding device provided with a board, etc., hereinafter expressed as being combined as a first-aid board or first-aid cabinet, all of which are available from Cederroth International AB, Sweden. The plaster packs used with Salvequick® plaster dispenser are particularly designed for accommodation in a Salvequick® plaster dispenser.

Consequently, it is extremely important that the first-aid products can be accessed quickly and easily in the event of an accident.

Existing plaster dispensers are encumbered with some problems.

A first problem is that a separate key in the form of a particularly designed plastic element, as mentioned above, is required to release plaster packs from the plaster dispenser. The reason for this is to prevent personnel in a workplace from taking plaster packs for private use. Normally, a responsible person is chosen in each workplace to restock the first-aid board and first-aid cabinet or the like. The risk with a separate key is that the key may be lost or simply disappear therewith preventing restocking of the dispenser.

When using said first-aid cabinet there is thus required two types of key, one key for unlocking the cabinet in order to take out replenishment products and a dispenser key for replacing empty packs with fresh packs.

Another problem is that the plasters may become soiled. The dispenser has a plastic cover that can be folded up from the part of the dispenser accommodating the plaster pack, wherein the cover is swung about an axis which extends along the rear long side of the dispenser so as to enable plasters to be taken therefrom. The cover is intended to prevent the plasters from being contaminated by undesirable particles, such as dust. When a person that has suffered a superficial wound goes to pick out a plaster, there is a risk that blood will drip from the wound down among the plasters. If the plaster dispenser is, instead, screwed upside down to the wall or to the first-aid board or to the first-aid cabinet, the cover, which is intended to keep the plaster dispenser sealed by abutment with the part of the dispenser that accommodates the plaster pack, will be weighted downwards, wherewith the bottom of the dispenser will be open. Consequently, the dispenser cannot be turned upside down in order to prevent blood from dripping down among the plasters, since dust is able to find its way in among the plasters when the cover is open.

An aim of the present invention is to solve these problems.

Accordingly, the present invention relates to a plaster dispenser from which plasters can be taken individually from a plaster pack that includes a number of plasters each inserted into a plastic or a paper pocket, wherein the pockets are directed in mutually the same direction, wherein the pockets are, together, surrounded by a folded sheet of plastic or paper, wherein the first edge of said sheet extends at right angles to the long direction of respective plaster pockets, wherein the plaster pack is widened from said first edge in a direction towards two mutually opposing second edges of said sheet parts, wherein the plaster dispenser includes a box-shaped space, and wherein the invention is characterised in that the box-shaped space is, in cross-section, comprised of two mutually parallel and generally vertical walls of which one, the rear wall, extends downwards in relation to a front wall, in that the rear wall includes at a height level lower than the lower edge of the front wall a generally horizontal rear shoulder, in that the upper edge of the rear wall is folded so as to provide a generally horizontal delimiting surface, in that the distance between said delimiting surface and said shoulder corresponds to the width of the sheet-part of the plaster pack in a direction parallel with the longitudinal extension of the plaster pockets, and in that the box-like shaped space is disposed so that the plasters can only be accessed from an opening formed in the front wall between the lower edge of said front wall and its web plane.

The invention will now be described in more detail partly with reference to exemplifying embodiments of the invention illustrated in the accompanying drawings, in which FIG. 1 is a sectioned side view of a plaster dispenser; and FIG. 2 illustrates a plaster dispenser mounted on a cabinet door, for instance, seen from the outside of the cabinet door.

FIG. 1 illustrates a plaster dispenser 1 for the removal of plasters 3 individually from the aforesaid, known plaster pack 2. The plaster pack 2 includes a plurality of plasters 3 which are each inserted into a plastic or paper pocket. These pockets are directed in mutually the same direction and are, together, surrounded by a folded plastic or paper sheet 4a, 4b respectively. The folded edge 5 of the sheet extends at right angles to the longitudinal direction of the plaster pockets. The plaster pack 2 is widened from said first edge 5 in a direction towards two mutually opposite second edges 19a, 19b of the sheet parts. The plaster dispenser 1 includes a box-shaped space 6.

In accordance with the invention, the box-shaped space 6 is comprised, in cross-section, of two mutually parallel and generally vertical walls. One wall 7, the rear wall, extends downwards in relation to a front wall 8. At a height level lower than the lower edge 9 of the front wall 8, the rear wall 7 is provided with a generally horizontal rear shoulder 10 against which the second edge 19a of the plaster pack 2 rests in the box-shaped space 6. The upper edge of the rear wall 7 is folded to form a generally horizontal delimiting surface 11, wherein the distance between said delimiting surface 11 and said shoulder 10 corresponds to the width of the sheet part 4a of the plaster pack 2 in a direction parallel with the longitudinal extension of the plaster accommodating pockets. The box-shaped space 6 is disposed so that the plasters 3 can only be accessed from an opening 16 formed in the front wall 8 between the lower edge 9 of the front wall 8 and the web plane 14 of said front wall 8.

According to one preferred embodiment of the invention, the front wall 8 has the form of a door, which can be locked to a cabinet in which the space 6 is located.

A surface 4a of the sheet part of the plaster pack 2 is thus in abutment with the rear wall 7, between the shoulder 10 and the delimiting surface 11.

In the case of one preferred embodiment, one generally horizontal rear shoulder 10 is positioned at the lower edge 12 of the rear wall 7 and a front generally horizontal shoulder 17 is placed at the lower edge 9 of the front wall 8.

When plasters 3 shall be removed from the plaster pack 2, this embodiment will provide additional support to the pack 2, by virtue of the second edge 19a of the pack 2 lying in abutment with the rear shoulder 10 and the second edge 19b of the plaster pack 2 lying in abutment with the front shoulder 17.

When a plaster 3 is taken from an opening 16 on the front side of a cabinet door 18 (see FIG. 2), it may happen that the plaster pack 2 is initially displaced upwards, due to the hand with which a plaster shall be removed knocking against the pack 2. This may result in the pack 2 being drawn downwards as the person pulls on the plaster. This happening is avoided by virtue of the first edge 5 lying generally in abutment with the delimiting surface 11, so as to prevent the plaster pack 2 from being dislodged upwards.

The plaster dispenser 1 is placed on the inner surface of the cabinet door 18, as seen from the front of the cabinet door 18. That part of the plaster dispenser 1 located behind the cabinet door 18 is marked with broken lines.

In order to join the rear wall 7 and the front wall 8 together, the rear wall 7 includes a planar portion 13 which projects out from its lower edge 12 and which slopes downwards and outwards to the web plane 14 of the front wall. An opening 16 is provided in the front wall 8 between the lower edge 9 of said front wall 8 and the web plane 14 of the front wall by a projecting planar part 13 from the lower edge 12 of the rear wall 7. The slope may vary between different plaster packs, depending on the configuration of the packs 2 used with the plaster dispenser 1 concerned.

The rear wall 7 includes at least one hole 15. Holes 15 in the rear wall 7 are shown in broken lines. The rear wall 7 will preferably include two mutually spaced holes 15 so as to enable the sheet-part 4a of the pack 2 that lies in abutment with the rear wall 7 in the box-shaped space 6 to be moved away from the rear wall 7 and therewith released from the delimiting surface 11. The holes 15 will conveniently have a diameter that is larger than the diameter of a pencil or a human finger so as to enable the pencil or the finger to pass readily through the hole 15; see FIG. 2. Subsequent to having inserted a finger through the hole 15, pressure is brought to bear on that sheet-part 4a of the pack 2 that lies against the rear wall 7 between the shoulder 10 and the delimiting surface 11, therewith releasing the sheet-part 4a of the plaster pack 2 from its placement between the shoulder 10 and the delimiting surface 11. The plaster pack 2 has therewith been loosened from the plaster dispenser 1 and can be lifted therefrom. This construction, or said holes 15, obviates the requirement of the special key described above.

When the space 6 cannot be locked in the described manner, due to the space, for instance, being located on the rear side of a lockable cabinet door, no finger hole 15 is included but instead, a number of smaller holes are provided in which a plastic key can be inserted from the outside of the rear wall 7 so as to displace the first edge 5 past the delimiting surface 11 and therewith enable the pack 2 to be drawn upwards.

The plasters 3 in the plaster pack 2 project forwardly in the opening 16. The plasters 3 in the pack 2 are placed for access in the opening 16 of the front wall 8.

According to one embodiment, the plaster dispenser 1 is constructed in the door 18 of a first-aid cabinet; see the broken lines in FIG. 2. When providing the dispenser with a new plaster pack 2, the pack is turned with the plasters 3 facing downwards. The plaster pack 2 is pushed down into the box-shaped space 6 in the dispenser 1, with the longer part of the sheet-part 4a of said pack 2 placed against the rear wall 7. The plaster pack 2 will then be positioned in place against the generally horizontal rear shoulder 10 or the rear 10 and the front shoulder 17, depending on the design of the dispenser 1. When the plaster pack 2 lies in place in the box-shaped space 6, the plasters 3 will be visible through the opening 16 and readily accessed by a person wishing to take a plaster 3.

When a pack 2 has been emptied and needs to be replaced with a fresh plaster pack 2, the person responsible will insert his/her fingers into the hole or the holes 15 provided in the rear wall 7 and therewith loosen the rear sheet-part 4a of the pack 2 from the delimiting surface 11 so that said empty pack can be moved upwards and out of the box-shaped space 6. The empty plaster pack 2 is therewith removed from the dispenser 1 and a new plaster pack 2 can be inserted.

According to another embodiment of the invention, there is provided a cover 20 which is pivotally mounted on a pivot axis 21 and which functions to cover the opening 16. The cover 20 can be swung about the pivot axis 21 from the opening 16 in accordance with the arrow shown in FIG. 1.

Although the invention has been described with reference to a number of exemplifying embodiments thereof, it will be understood that the plaster dispenser 1 including rear and front wall 7 and 8 respectively including the delimiting surface 11 of the rear wall 7 and the shoulders 10, 17 may have other appropriate designs without departing from the basic concept of the invention.

The invention is therefore not restricted to the aforedescribed exemplifying embodiments thereof since variations and modifications can be made within the scope of the accompanying Claims.

The invention claimed is:

1. A plaster dispenser for removing plasters individually from a plaster pack, wherein the plaster pack comprises a plurality of plasters, and a plurality of plaster accommodating plastic or paper pockets, each plaster inserted in a respective one of said plastic or paper pockets, the plastic or paper pockets extending in a common direction, and the plastic or paper pockets being together surrounded by a folded plastic or paper sheet, the sheet comprising a folded first edge extending at right angles to the common direction of the pockets, and the plaster pack comprising a pair of sides diverging from said first edge in a direction towards two opposing second edges of said folded sheet, the plaster dispenser comprises a box-shaped space, the box-shaped space is comprised in cross-section of two parallel and generally vertical walls, the two walls being a front wall and a rear wall, wherein the front wall comprises an opening formed between a lower edge of the front wall and a web plane of the front wall, the rear wall extends downwards in relation to the front wall, the rear wall is provided with a generally horizontal rear shoulder at a height level lower than the lower edge of the front wall, an upper edge of the rear wall is folded to form a generally horizontal delimiting surface, the distance between the delimiting surface and the rear shoulder corresponds to the length of one of said sides of the plaster pack in a direction parallel to said common direction, and the box-shaped space is disposed so that the plasters can only be accessed from the opening formed in the front wall.

2. The plaster dispenser according to claim 1, wherein the lower edge of the front wall comprises a generally horizontal front shoulder which projects out into the box-shaped space.

3. The plaster dispenser according to claim 2, wherein the one of the two opposing second edges is in abutment with the generally horizontal front shoulder.

4. The plaster dispenser according to claim 2, wherein the rear wall comprises a planar part which projects out from the lower edge of said rear wall and which slopes downwards and outwards to the web plane of the front wall.

5. The plaster dispenser according to claim 2, further comprising at least one hole located in the rear wall.

6. The plaster dispenser according to claim 2, wherein the plasters in the plaster pack are disposed so as to be accessible in the opening of the front wall.

7. The plaster dispenser according to claim 2, wherein said first edge is in abutment with the delimiting surface.

8. The plaster dispenser according to claim 2, wherein one of the two opposing second edges is in abutment with the generally horizontal rear shoulder.

9. The plaster dispenser according to claim 2, wherein one of the two opposing second edges is in abutment with the generally horizontal front shoulder.

10. The plaster dispenser according to claim 2, further comprising a plurality of small holes in the rear wall, and in which wherein a plastic key can be inserted in the holes so as to move the first edge past the delimiting surface and therewith enable the plaster pack to be drawn upwards.

11. The plaster dispenser according to claim 1, wherein the rear wall comprises a planar part which projects out from a lower edge of said rear wall and which slopes downwards and outwards to the web plane of the front wall.

12. The plaster dispenser according to claim 11, further comprising at least one hole located in the rear wall.

13. The plaster dispenser according to claim 11, wherein the plasters in the plaster pack are disposed so as to be accessible in the opening of the front wall.

14. The plaster dispenser according to claim 11, wherein said first edge is in abutment with the delimiting surface.

15. The plaster dispenser according to claim 11, wherein one of the two opposing second edges is in abutment with the generally horizontal rear shoulder.

16. The plaster dispenser according to claim 1, further comprising at least one hole located in the rear wall.

17. The plaster dispenser according to claim 1, wherein the plasters in the plaster pack are disposed so as to be accessible in the opening of the front wall.

18. The plaster dispenser according to claim 1, wherein said first edge is in abutment with the delimiting surface.

19. The plaster dispenser according to claim 1, wherein one of the two opposing second edges is in abutment with the generally horizontal rear shoulder.

20. The plaster dispenser according to claim 1, further comprising a plurality of small holes in the rear wall, wherein a plastic key can be inserted in the holes so as to move the first edge past the delimiting surface and therewith enable the plaster pack to be drawn upwards.

* * * * *